(12) United States Patent
Patel et al.

(10) Patent No.: US 7,767,870 B2
(45) Date of Patent: Aug. 3, 2010

(54) RISER TERMINATION DEVICES FOR REDUCED CATALYST ATTRITION AND LOSSES

(75) Inventors: Rutton D. Patel, Arlington, VA (US); Arun K. Sharma, Alexandria, VA (US); E. Nicholas Jones, Baton Rouge, LA (US); James H. Beech, Jr., Kingwood, TX (US); Richard E. Walter, Long Valley, NJ (US); Donald F. Shaw, Denville, NJ (US); Kenneth R. Clem, Humble, TX (US); Nicolas P. Coute, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1183 days.

(21) Appl. No.: 11/216,652

(22) Filed: Aug. 31, 2005

(65) Prior Publication Data

US 2007/0049782 A1    Mar. 1, 2007

(51) Int. Cl.
*B01J 8/18* (2006.01)
*C07C 1/00* (2006.01)

(52) U.S. Cl. .......... 585/639; 422/139; 422/143; 422/144; 422/145; 422/147

(58) Field of Classification Search ........... 585/639; 502/208; 422/139, 143, 144, 145, 147
See application file for complete search history.

(56) References Cited

U.S. PATENT DOCUMENTS

| | | | |
|---|---|---|---|
| 4,313,910 A | 2/1982 | Dries et al. | 422/147 |
| 4,404,095 A | 9/1983 | Haddad et al. | 208/161 |
| 4,664,888 A * | 5/1987 | Castagnos, Jr. | 422/147 |
| 4,711,712 A | 12/1987 | Schatz | 208/153 |
| 5,190,650 A | 3/1993 | Tammera et al. | 210/256 |
| 2004/0076554 A1 | 4/2004 | Kuechler et al. | 422/139 |
| 2004/0121902 A1* | 6/2004 | Chang et al. | 502/208 |

\* cited by examiner

*Primary Examiner*—Glenn Caldarola
*Assistant Examiner*—Prem C. Singh
(74) *Attorney, Agent, or Firm*—Kevin M. Faulkner; Frank E. Reid

(57) ABSTRACT

A gas-solids reaction system with termination devices to connect a riser with one or more separation devices. The termination devices have a radius of curvature that is at least 1.0 times as great as the diameter of the conduit forming the termination device. The termination devices can be openly or closely coupled to the separation devices.

13 Claims, 10 Drawing Sheets

RISER TERMINATION DEVICES FOR REDUCED CATALYST ATTRITION AND LOSSES

FIELD OF THE INVENTION

This invention is directed to an apparatus and method for separating solid catalyst particles from a gas-solids flow. In particular, this invention is directed to riser termination devices that reduce catalyst attrition and losses as well as methods for performing gas-solids reactions in risers having the termination devices.

BACKGROUND OF THE INVENTION

Fluid-solid reaction systems, such as gas-solids reaction systems, often require the solids to be retained in early stages of the reaction system while the vapor product, essentially free of solids, is processed in downstream equipment. It is desirable in these systems that the solids be as completely removed as possible from the vapor before transferring the vapor to the downstream equipment. In reaction systems that use small particle catalysts, the loss of catalyst particles during operation means that additional catalyst has to be added during operation to make up for the catalyst loss. Particularly in cases where the cost of catalyst is high, even marginal improvements in solid particle retention can lead to substantial reductions in operating costs. The problem of solid particle loss can be compounded if the solid particles are susceptible to attrition, such as by shattering or otherwise breaking into smaller pieces. Smaller particles are typically more difficult to separate from a gas-solids flow, so the attrition of large particles into smaller particles compounds the problem of effectively separating solids from a gas flow. As a result, reactor designs and separation methods that tend to reduce particle attrition while improving separation efficiency are desirable.

U.S. Patent Application Publication 2004/0076554 describes a riser reactor system having multiple risers that feed into a separation vessel. The multiple risers are located outside of the separation vessel. The top of each riser is connected to the separation vessel using a single deflecting member in the form of a curved or angled connector.

U.S. Pat. No. 4,664,888 describes a riser reactor that feeds a gas-solids flow into a separation vessel through a plurality of rough cut separators. Each of the rough cut separators cause the output of the riser to undergo a tight, 180 degree downward turn after exiting the riser.

U.S. Pat. No. 4,313,910 describes a riser reactor that feeds into a separation vessel after being deflected by a semicircular cap. A substitute gas is introduced into the gas-solids flow in the semicircular cap to replace the gas from the riser reactor.

U.S. Pat. No. 5,190,650 describes a riser having a plurality of openings around the circumference of the riser at its discharge end. The openings in the riser are allow gas to escape tangentially from the riser. Gas discharged through an opening passes through a curvilinear tube and tangentially enters a cyclone separator.

What is needed is a system and method for reducing or minimizing the attrition and loss of solid particles during separation from a gas-solids flow. The system and method should be compatible with conventional riser designs as well as conventional separators, such as cyclone separators. The system and method should also allow a gas-solids flow from a riser to be closely coupled with multiple separation devices, such as cyclone separators.

SUMMARY OF THE INVENTION

This invention provides a method and apparatus for separating solids from a gas flow in a gas-solids reaction system while reducing or minimizing the solid attrition and/or loss of solids from the reaction system. In an embodiment, the invention provides a method for separating solids from a gas-solids flow. The method begins by flowing a gas-solids flow in a riser, where the top of the riser is joined to a plurality of termination devices. The gas-solids flow is then passed through the plurality of termination devices into one or more separation devices. The radius of curvature of each termination device is from about 1.0 to 5 times greater than the diameter of the termination device. The gas-solids flow is then separated into a lower density flow and a higher density flow in the one or more separation devices.

In another embodiment, the invention provides an apparatus for performing an oxygenate to olefin conversion reaction. The apparatus includes a riser for performing a gas-solids reaction, the riser having at least one solids inlet and at least one feedstock inlet. The apparatus also includes a plurality of arcuate conduits connected to the top of the riser, each conduit forming an arc of from 75° to 105° and having a radius of curvature of from about 1.0 to 5 times greater than the diameter of the conduit. The apparatus further includes one or more separation devices, such as cyclone separators, for receiving a gas-solids flow from the riser via the arcuate conduits.

In still another embodiment, the invention provides a method for separating solids from a gas-solids flow. The method begins flowing a gas-solids flow in a riser, where the top of the riser is joined to a plurality of termination devices. The gas-solids flow is then passed out of the riser and through a plurality of termination devices that openly couple the riser to one or more separation devices, the combined cross-sectional area of the termination devices being at least 100% of the cross-sectional area of the riser. The gas-solids flow is then separated into a higher density flow and a lower density flow in the one or more separation devices

BRIEF DESCRIPTION OF THE DRAWINGS

Various embodiments of the invention are also described in the accompanying drawings, wherein.

DETAILED DESCRIPTION OF THE INVENTION

Figure 1:
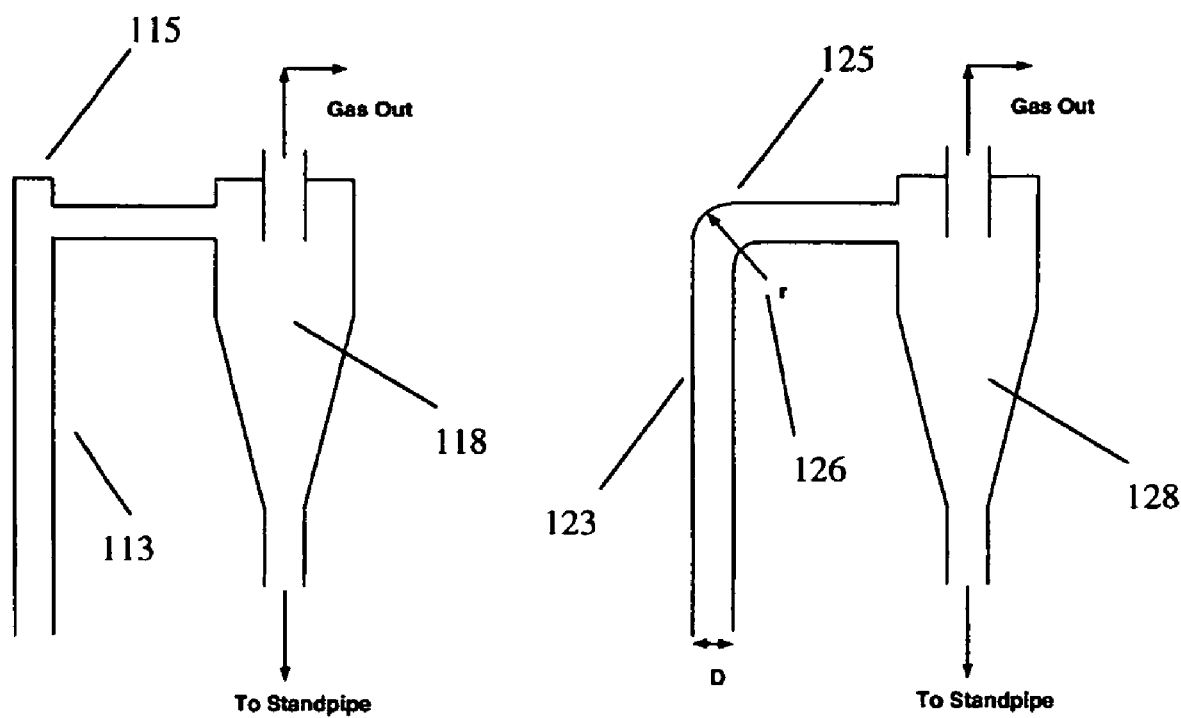
FIG. 1 schematically shows examples of termination devices for connecting a riser to a separation device.

I. Reducing Catalyst Attrition and Loss by Transferring a Gas-Solids Flow to a Separator Through a Termination Device This invention provides a method and apparatus for separating solids (such as catalyst) from a gas flow in a gas-solids reaction system while minimizing attrition and loss of the solids. This is achieved by coupling a riser to one or more separation devices using termination devices which reduce solid attrition. This assists in reducing the amount of solids that are lost due to incomplete separation of solids from the gas flow.

In an embodiment, a gas-solids flow leaving a riser is transferred to a plurality of separation devices via a plurality of arcuate or curved conduits. The arcuate conduits serve as termination devices that closely couple the riser to a plurality of separation devices, such as cyclone separators. The arcuate conduits are connected to the riser at the top of the riser. Each of the arcuate conduits has an external radius of curvature that is from 1.0 to 5 times as large as the diameter of the conduit. These arcuate conduits allow a gas-solids flow to be transferred from the riser to the separation devices while reducing or minimizing solid particle losses, such as losses due to attrition of the solid particles. In a preferred embodiment, the arcuate conduits provide a 90° change in the flow direction of the gas-solids flow.

In another embodiment, gas-solids flow is transferred from a riser to a separation volume or other disengaging vessel via one or more non-close coupled termination devices. The gas-solids flow exits the riser at the top of the riser and is deflected or guided into the separation volume by the termination devices. The solids are then separated from the gas by separation devices contained within the separation volume. The combined cross-sectional area of the termination devices for accommodating the gas solids flow is at least 100% of the cross-sectional area of the riser. The termination devices allow a gas-solids flow to be transferred from the riser to the separation volume while reducing or minimizing solid particle losses, such as losses due to attrition of the solid particles.

II. Connecting a Riser to a Separation Device in a Reaction System

In various embodiments, riser reactors can be used to perform a variety of gas-solids reactions. Generally, solid particles for catalyzing a reaction are introduced into the riser. A reactive feedstock is then flowed into the riser and through the solid particles. As the feedstock reacts and flows up through the riser, solid particles become entrained in the feedstock flow. The solid particles are then preferably removed from the gas-solids flow after exiting the riser. In an embodiment, the riser can have a diameter of at least 1 meter, or at least 1.5 meters, or at least 2 meters, or at least 3 meters, or at least 4 meters, or at least 5 meters, or at least 6 meters. In another embodiment, the riser can have a diameter of 9 meters or less, or 8 meters or less, or 7 meters or less, or 6 meters or less, or 5 meters or less, or 4 meters or less. Note that the diameter of the riser can vary over the length of the riser. For the purposes of this invention, the diameter of the riser refers to the diameter of the riser at the location where the riser is joined to a termination device.

After the gas-solids flow leaves the riser, the solid particles are removed from the gas-solids flow by passing the mixture of gas and solids through one or more separation devices, such as cyclone separators. To increase the efficiency of removal, the gas-solids flow can be passed through multiple stages of separators.

In an embodiment, a gas-solids flow can be transferred from a riser to a separation device by closely coupling the riser to one or more separators. The riser can be closely coupled to a separator by providing one or more closed conduits between the riser and one or more separators. Alternatively, two or more closed conduits can be provided, or three or more closed conduits, or four or more closed conduits. In a preferred embodiment, the closed conduits are substantially sealed to prevent losses from the gas-solids flow to the surrounding environment prior to entering the first separator, with only a small vent gap placed between the riser termination device and the first separation device or placed between the first and second separation devices to allow reactor vessel vapors to escape. For practical reasons, a closed conduit exiting from the top of a riser reactor should have a curved geometry in order to redirect the gas-solids flow prior to entering a separator device or a disengaging volume. The closed conduit can redirect the gas-solids flow by up to 45°, or by up to 60°, or by up to 75°, or by up to 90°, or by up to 120°, or by up to 150°. Alternatively, the closed conduit can redirect the gas-solids flow by 180° or less, or by 150° or less, or by 120° or less, or by 105° or less, or by 90° or less.

In a preferred embodiment, each closed conduit has the form of a bend or elbow that has a radius of curvature. The radius of curvature for a conduit is measured along outer surface of the bend in the conduit, as opposed to the centerline of the conduit or the inner surface of the bend. In an embodiment, the radius of curvature of the conduit is at least 1.0 times as large as the diameter of the conduit, or at least 1.75 times as large, or at least 2 times as large, or at least 2.5 times as large, or at least 3 times as large. Alternatively, the radius of curvature of the conduit is up to 5 times as large as the diameter of the conduit, or up to 4 times as large, or up to 3 times as large, or up to 2.5 times as large. In another embodiment, the diameter of the conduit can be 0.25 times the diameter of the riser or more, or 0.35 times or more, or 0.4 times or more. In still another embodiment, the diameter of the conduit can be up to 1.0 times the diameter of the riser, or 0.5 times the diameter of the riser, or up to 0.4 times the diameter.

FIG. 1 schematically shows an example of a conventional "blind-tee" riser termination device 115, which does not have a well-defined radius of curvature, and an elbow termination device 125 having a radius of curvature 126 for redirecting a gas-solids flow from a riser into a separation device. Note that radius of curvature 126 is measured relative to the outer surface of the bend in the conduit. In FIG. 1, the gas-solids flow proceeds up through riser 113 or 123 until it reaches a termination device, either blind-tee terminator 115 or elbow terminator 125. The terminator redirects the gas-solids flow into separation device 118 or 128, which is shown here as a cyclone separator.

Figure 2:
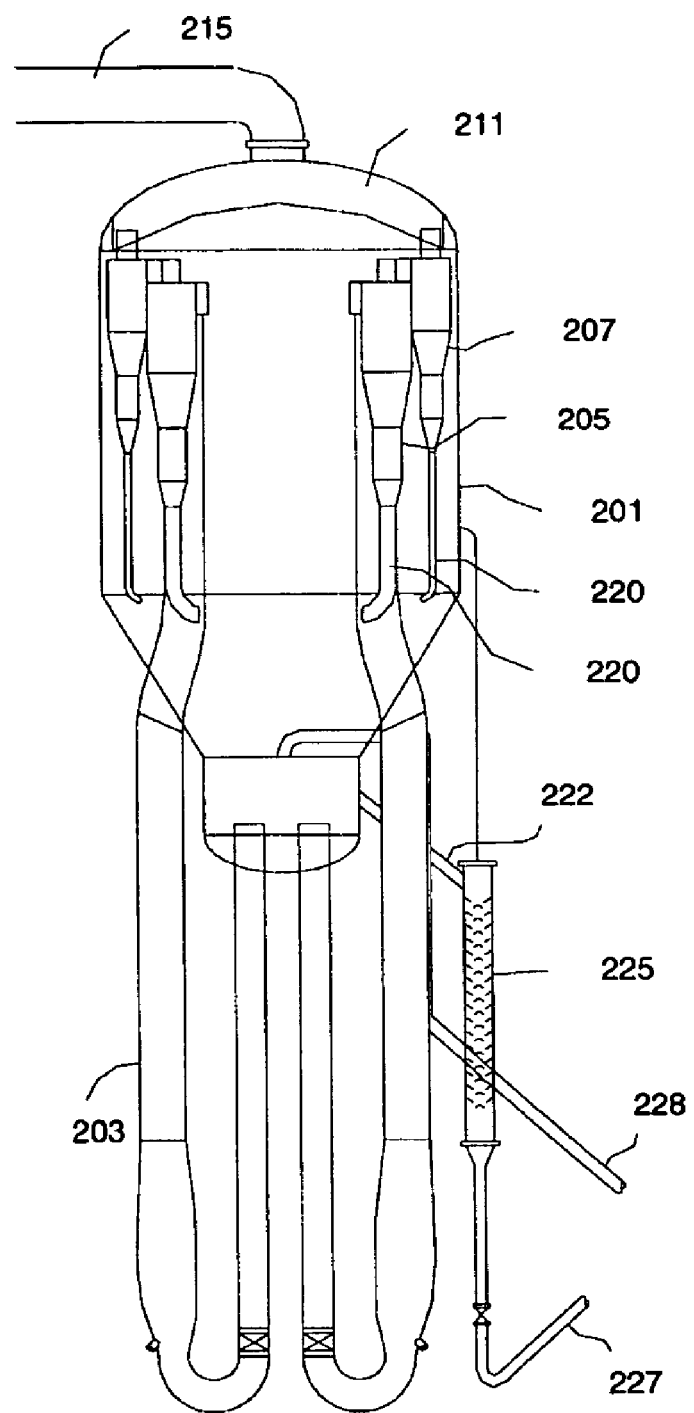
FIG. 2 depicts a schematic of a reactor including termination devices according to an embodiment of the invention.

FIG. 2 shows a schematic example of a reaction system having a riser reactor with riser termination devices that are closely coupled to a plurality of separators in accordance with an embodiment of the invention. In FIG. 2, a vessel 201 surrounds the upper terminal end of a riser 203 which is closely coupled to two primary cyclones 205. In this embodiment, primary cyclones 205 are also closely coupled to secondary cyclones 207. Overhead gas from the secondary cyclone 207 exits the vessel 201 by means of an overhead plenum 211. This gas can then flow through conduit 215 for further processing, such as to recover a desired reaction product and/or to remove any additional solid particles still entrained in the gas flow. Solid particles (catalyst) recovered by the cyclones 205 and 207 drops through cyclone diplegs 220 into a solid particle bed in the lower portion of vessel 201. The solid particles can be drawn out of vessel 201 via conduit 222 into catalyst stripper 225. After passing through stripper 225, solid particles can then flow to a regeneration system (not shown) via conduit 227. After regeneration, solid particles returned to the vessel 201 via conduit 228.

Figure 3A:
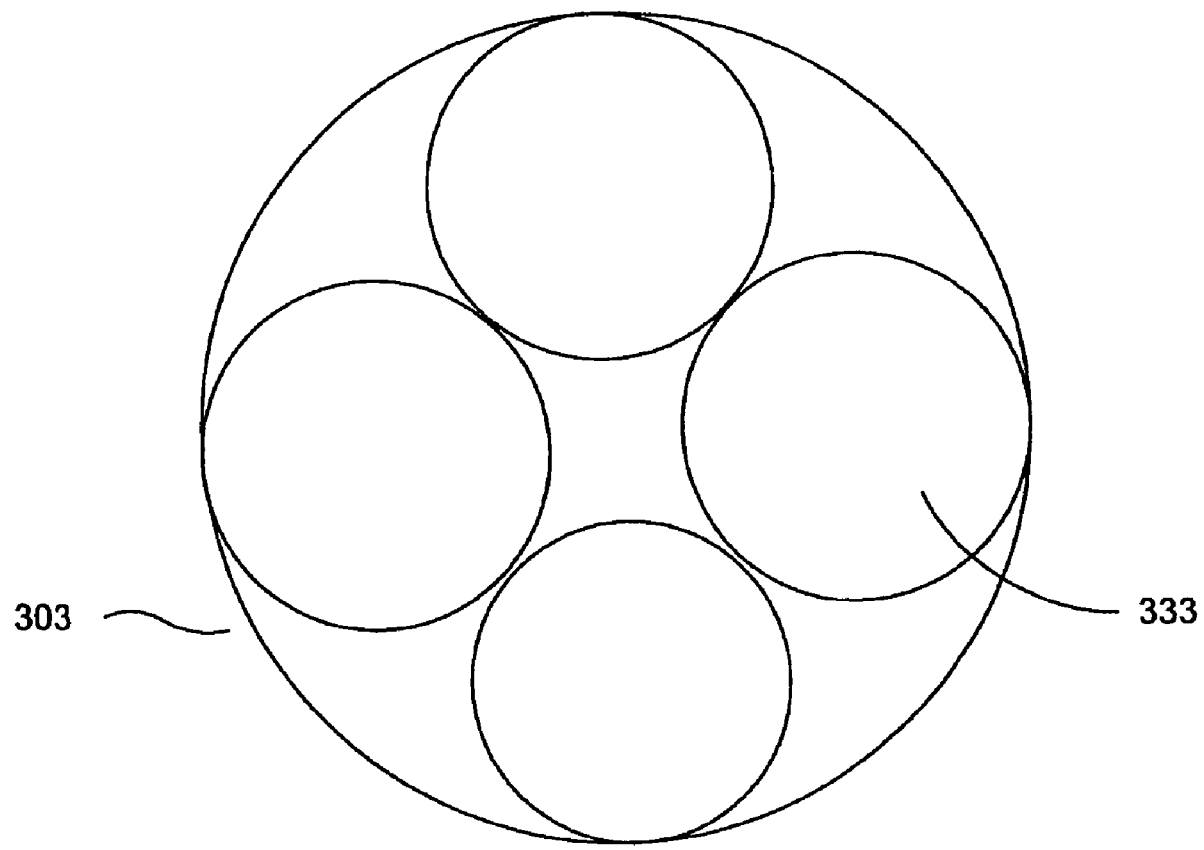
FIGS. 3a and 3b schematically show a top cutaway view and a side view, respectively, of a riser with termination devices according to an embodiment of the invention.
Figure 3B:
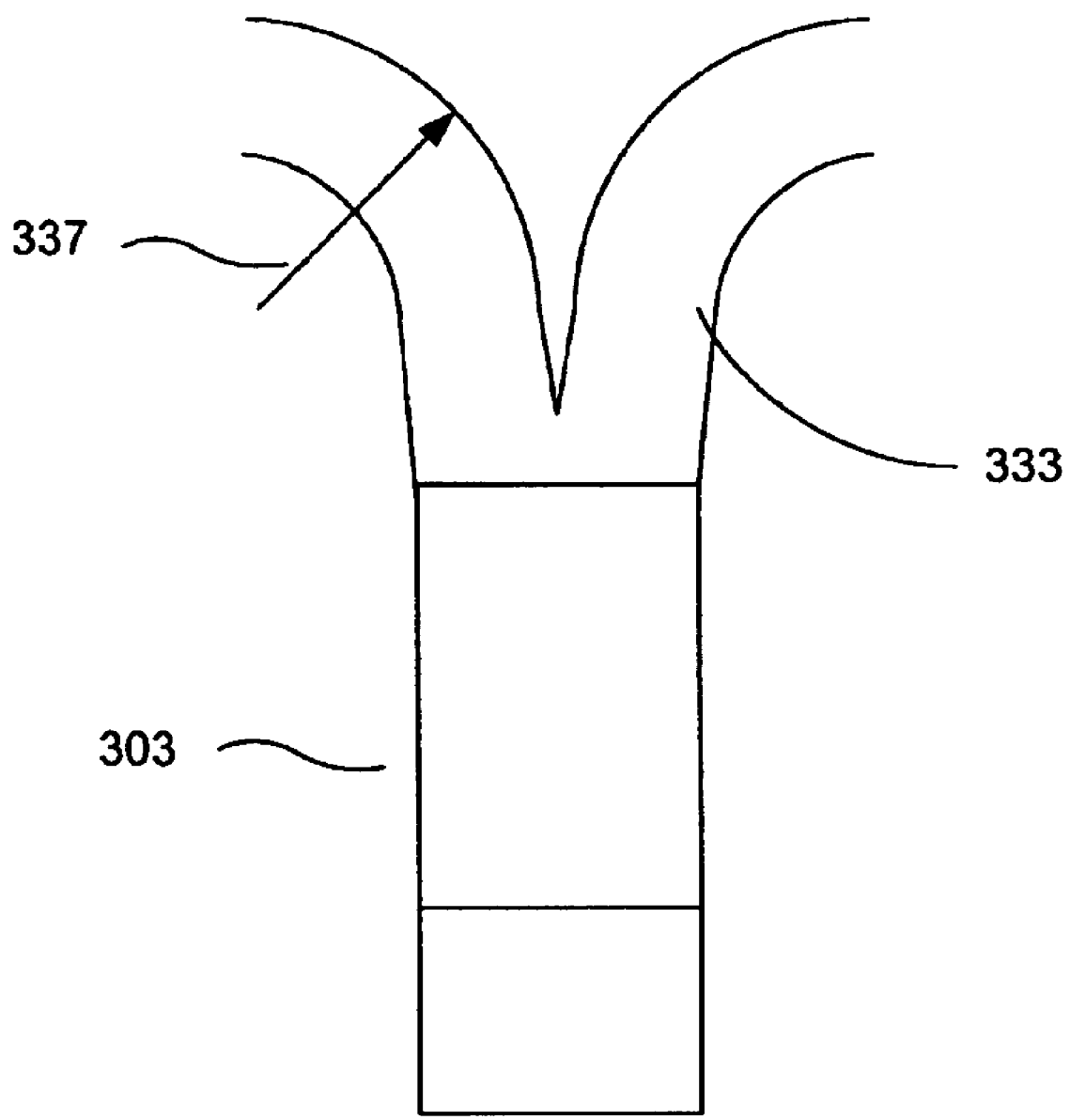

FIGS. 3a and 3b schematically depict a connector for closely coupling a riser to a plurality of separation devices. FIG. 3a shows a top sectional view of an embodiment where 4 arcuate conduits are arranged for receiving a gas-solids flow from a riser. FIG. 3b shows a corresponding side view of the arcuate conduits. In FIGS. 3a and 3b, arcuate conduits 333 are connected to the top of riser 303. Each conduit 333 has a radius of curvature 337 which is preferably from 1.0 to 5 times greater than the diameter of riser 303. As shown in FIG. 1b, radius of curvature 337 is measured relative to the outer surface of the bend of conduit 333. In a preferred embodiment, each conduit 333 would connect riser 303 to a different primary separation device. For example, in such a preferred embodiment, riser 303 would be closely coupled to 4 arcuate conduits 333, which would also be closely coupled to 4 primary cyclones.

At the location where riser 303 and conduits 333 come together, the overall width of the structure begins to increase due to the divergence of the conduits. As the conduits begin to separate, a gap is left behind between the conduits. Alternatively, the space between the conduits can contain a solid central portion, such as a space-filling solid central portion. As shown in FIG. 3b, the gap between the conduits does not necessarily form at the junction between the conduits 333 and the riser 303. Instead, the gap (or filled in solid central portion) can begin above the junction.

Figure 4A:
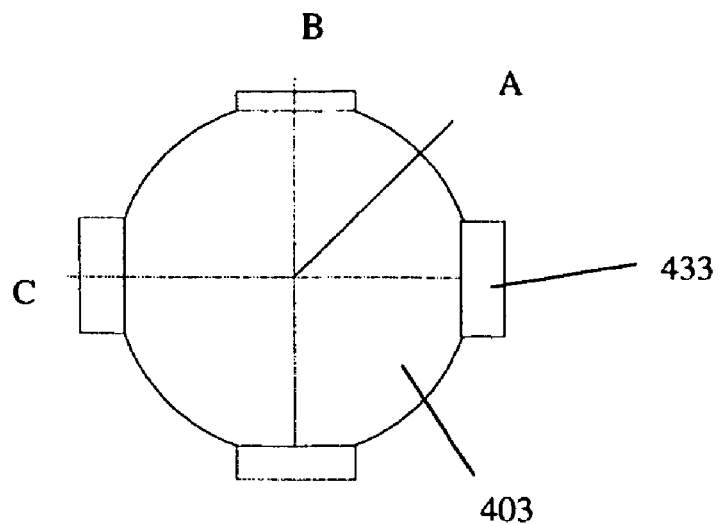
FIGS. 4a, 4b, and 4c schematically show a profile of the connection between termination devices and a riser according to an embodiment of the invention.
Figure 4B:
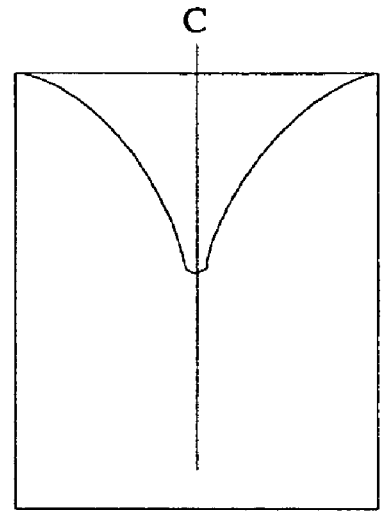
Figure 4C:
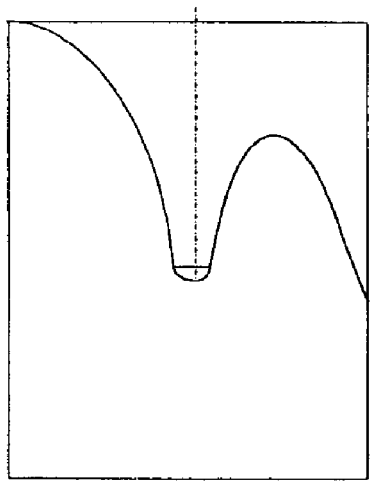

FIGS. 4a-4c schematically shows the interior shape of the connection between a riser and 4 arcuate conduits in an embodiment of the invention. FIG. 4a shows a top view of riser 403 connected to 4 conduits 433. FIG. 4b shows a profile of the shape of the connecting region between the riser and the conduits along a line C from the exit of one conduit to the exit of an opposing conduit. FIG. 4c shows a profile of the shape of the connecting region between the riser and the conduits along a line from the exit of a conduit to the line denoted "Section A" in FIG. 4a. Conduits according to an embodiment of the invention having the profile shown in FIGS. 4a-4c provide a smooth 90° transition for gas exiting a riser. For conduits having such profiles, gas exiting through the top of the riser is diverted into one of the four conduits. The conduits are separated by walls between each conduit which meet in a solid central portion. In an embodiment, a geometry such as the shapes described in FIGS. 4a-4c can be formed from cast refractory metal components, formed metal components, or a combination of cast refractory and formed metal components.

In an alternative embodiment, a termination device for a riser can be openly coupled (or non-closely coupled) to one or more separation devices. The termination device can be openly coupled to a separation device by allowing the gas-solids flow exiting the riser to enter a disengaging volume that surrounds the riser. One or more separation devices for separating gas from solids are also enclosed in the disengaging volume.

In such an embodiment, one or more termination devices can be openly coupled to the separation devices in the disengaging volume. Various types of termination devices can be used, so long as the termination devices also have a radius of curvature that is greater than the diameter of the riser. Suitable termination devices can include curved deflector cap type termination devices. Alternatively, curved or arcuate conduits can be used without closely coupling the curved or arcuate conduit to a separation device. For example, the inlet of the arcuate conduit can be sealed to the top of the riser while the outlet allows a gas-solids flow to enter a disengaging volume containing one or more separators. In embodiments where the termination device has a defined conduit, the radius of curvature of the termination device is at least 1.0 times as large as the diameter of the conduit, or at least 1.75 times as large, or at least 2 times as large, or at least 2.5 times as large, or at least 3 times as large. Alternatively, the radius of curvature of the termination device is up to 5 times as large as the diameter of the conduit, or up to 4 times as large, or up to 3 times as large, or up to 2.5 times as large. In another embodiment, the termination device may not have a well-defined conduit size, such as the curved cap terminator shown in FIG. 5a. In such an embodiment, the diameter of the conduit can be defined as the maximum size of the connection between the termination device and the riser.

Figure 5:
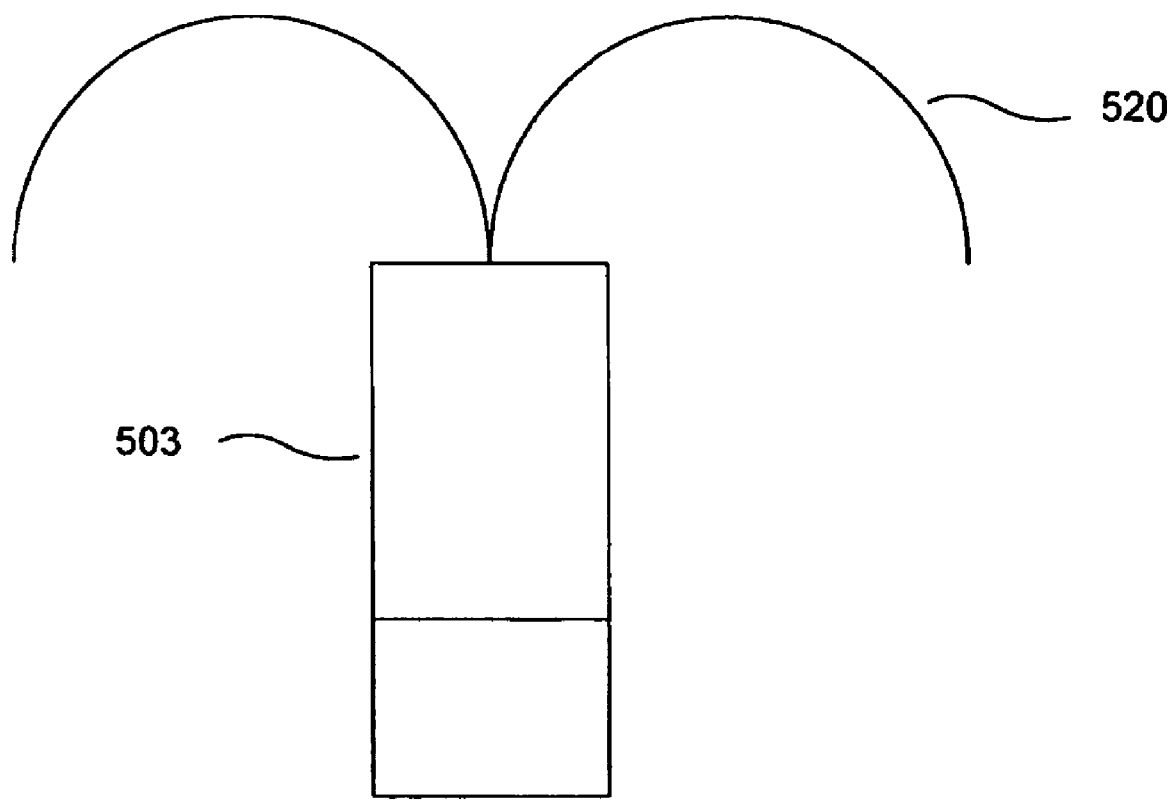
FIG. 5 schematically shows a termination device according to an embodiment of the invention.

FIG. 5 schematically depicts an example of a termination device openly coupled to one or more separation devices according to embodiments of the invention. FIG. 5 shows curved cap termination devices 520 where the gas-solids flow from the riser 503 is divided into the various curved cap terminators 520 as the flow exits the riser.

In still another embodiment, the invention provides another method for transferring a gas-solids flow is transferred from a riser to a separation volume or other disengaging vessel via one or more openly coupled termination devices having a combined cross-sectional area that is greater than the cross-sectional area of the riser. Suitable termination devices can include curved surface plate, deflector plate, and curved cap type termination devices. In an embodiment, the combined cross-sectional area of the termination devices is at least 100% of the cross-sectional area of the riser, or at least 175%, or at least 200%, or at least 250%, or at least 300%. Alternatively, the combined cross-sectional area of the termination devices is 350% of the cross-sectional area of the riser or less, or 300% or less, or 250% or less. In such an embodiment, the cross-sectional area of the termination devices is defined as the area of the cross-section where the gas-solids flow is no longer constrained by the surfaces of the termination device. The cross-sectional area of the riser is defined relative to the diameter of the riser at the top of the riser.

Figure 6A:
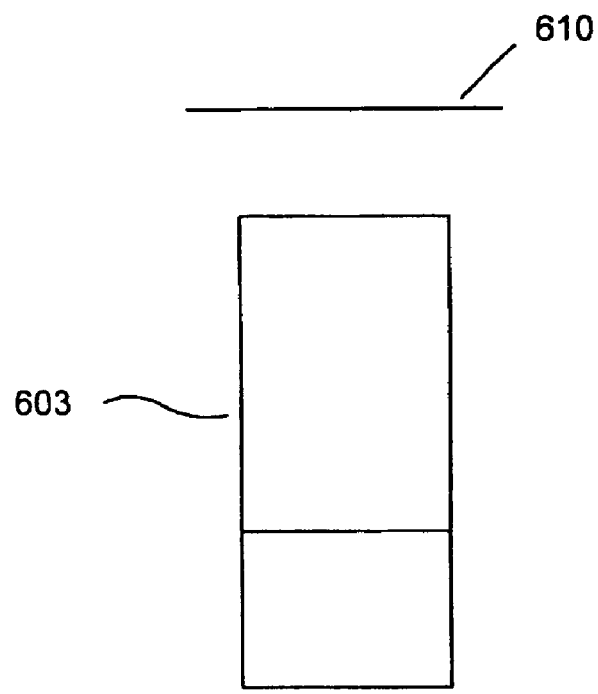
FIG. 6 schematically shows several types of termination devices for openly coupling a riser to a separation device.
Figure 6B:
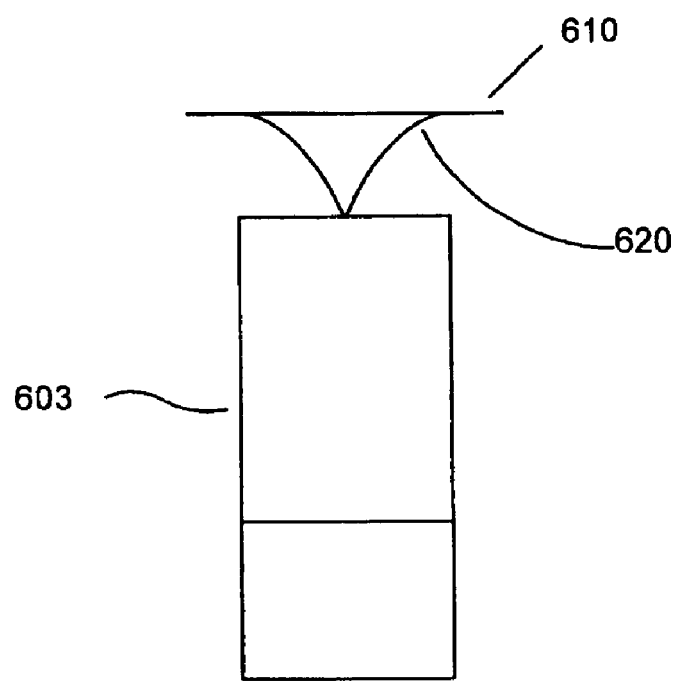
Figure 6C:
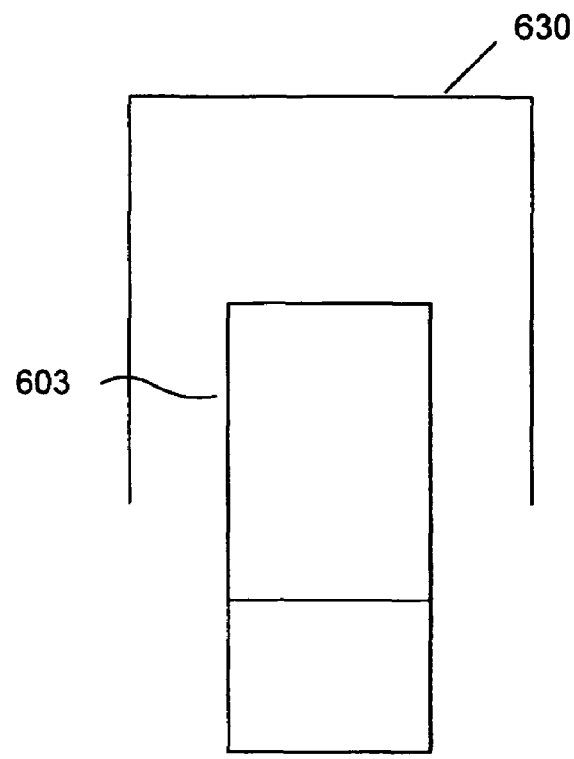
Figure 6D:
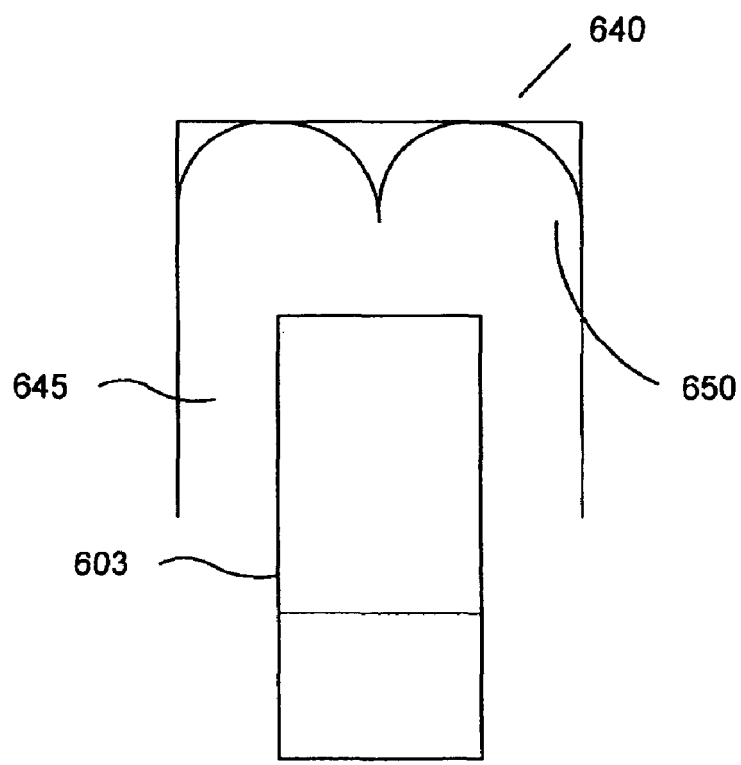

FIGS. 6a, 6b, 6c, and 6d schematically depict embodiments of termination devices openly coupled to the top of a riser. In FIG. 6a, riser 603 is terminated with a flat deflector plate termination device 610. The diameter of the plate is greater than the diameter of the riser. In this embodiment, the cross-sectional area of the exit of termination device is defined by the deflector plate and the edge of the riser. FIG. 6b depicts a curved surface plate termination device. Preferably, the curved surface 620 protruding from plate 610 can be formed from a refractory material. FIG. 6c depicts a cap deflector plate termination device. In FIG. 6c, the termination device 630 extends down past the top of riser 603 to create an annular exit area 635 for the gas-solids flow. FIG. 6d depicts a curved cap termination device 640 which has both curved surfaces 650 as well as an annular exit area 645. In a preferred embodiment, an termination device for openly coupling the riser to one or more separation devices incorporates both a curved surface and has a cross-sectional exit area of 100% or more of the riser cross-sectional area.

III. Types of Reaction Systems

The conduits, termination devices, and methods for connecting risers to separation devices according to this invention are useful in any reaction system for performing reactions involving solid particles entrained in a gas-solids flow. Non-limiting examples of such reaction systems include reaction systems selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates (e.g., alcohols) to olefins, systems for converting oxygenates (e.g., alcohols) to aromatics or gasoline, systems for oligomerizing olefins, and systems for converting unsaturated hydrocarbons to aldehydes. More specifically, such examples include:

A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (time of contact of feed and/or product with catalyst) from about 10 milliseconds to about 10 seconds;

B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 $hr^{-1}$ to about 100 $hr^{-1}$;

C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 $hr^{-1}$ to about 100 $hr^{-1}$, and an aromatic hydrocarbon/polyalkylaromatic hydrocarbon mole ratio of from about 1/1 to about 16/1;

D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 $hr^{-1}$ to about 200 $hr^{-1}$, and a hydrogen/hydrocarbon mole ratio of from about 0 to about 100/1;

E) The catalytic dewaxing of hydrocarbons by selectively removing straight chain paraffins. The reaction conditions are dependent in large measure on the feed used and upon the desired pour point. Typical reaction conditions include a temperature between about 200° C. and 450° C., a pressure of up to 3,000 psig and a liquid hourly space velocity from 0.1 $hr^{-1}$ to 20 $hr^{-1}$.

F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 100 $hr^{-1}$, and an aromatic hydrocarbon/alkylating agent mole ratio of from about 1/1 to about 20/1;

G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$, and an aromatic hydrocarbon/olefin mole ratio of from about 1/1 to about 20/1. The resulting products from the reaction are long chain alkyl aromatics, which when subsequently sulfonated have particular application as synthetic detergents;

H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$;

I) The hydrocracking of heavy petroleum feedstocks, cyclic stocks, and other hydrocrack charge stocks. The catalyst will contain an effective amount of at least one hydrogenation component;

J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 psig to about 800 psig, a WHSV-olefin from about 0.4 $hr^{-1}$ to about 0.8 $hr^{-1}$, a WHSV-reformate of from about 1 $hr^{-1}$ to about 2 $hr^{-1}$ and, optionally, a gas recycle from about 1.5 to about 2.5 vol/vol fuel gas feed;

K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 100° C. to about 400° C. and pressures from about 50 psig to 450 psig;

L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 $hr^{-1}$ to about 10 $hr^{-1}$;

M) The conversion of light paraffins to olefins and/or aromatics. Typical reaction conditions include temperatures from about 425° C. to about 760° C. and pressures from about 10 psig to about 2000 psig;

N) The conversion of light olefins to gasoline, distillate and lube range hydrocarbons. Typical reaction conditions include temperatures of from about 175° C. to about 375° C., and a pressure of from about 100 psig to about 2000 psig;

O) Two-stage hydrocracking for upgrading hydrocarbon streams having initial boiling points above about 200° C. to premium distillate and gasoline boiling range products or as feed to further fuels or chemicals processing steps. Either stage of the two-stage system can contain catalyst, which contains molecular sieve that is susceptible to loss of catalytic activity due to contact with water molecules. Typical reaction conditions include temperatures of from about 315° C. to about 455° C., pressures of from about 400 to about 2500 psig, hydrogen circulation of from about 1000 SCF/bbl to about 10,000 SCF/bbl and a liquid hourly space velocity (LHSV) of from about 0.1 $hr^{-1}$ to 10 $hr^{-1}$;

P) A combination hydrocracking/dewaxing process in the presence of a catalyst that contains molecular sieve that is susceptible to loss of catalytic activity due to contact with water molecules. The catalyst generally further comprises a hydrogenation component. Optionally included in the catalyst is zeolite molecular sieve such as zeolite Beta. Typical reaction conditions include temperatures from about 350° C. to about 400° C., pressures from about 1400 psig to about 1500 psig, LHSVs from about 0.4 $hr^{-1}$ to about 0.6 $hr^{-1}$ and a hydrogen circulation from about 3000 to about 5000 SCF/bbl;

Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-zeolite) from about 0.1 $hr^{-1}$ to about 200 $hr^{-1}$ and an alcohol to olefin molar feed ratio from about 0.1/1 to about 5/1;

R) The disproportionation of aromatics, e.g., the disproportionation toluene to make benzene and paraxylene. Typical reaction conditions include a temperature of from about 200° C. to about 760° C., a pressure of from about atmospheric to about 60 atmosphere (bar), and a WHSV of from about 0.1 $hr^{-1}$ to about 30 $hr^{-1}$;

S) The conversion of naphtha (e.g., $C_6$-$C_{10}$) and similar mixtures to highly aromatic mixtures. Thus, normal and slightly branched chained hydrocarbons, preferably having a boiling range above about 40° C., and less than about 200° C., can be converted to products having a substantially higher octane aromatics content by contacting the hydrocarbon feed with a molecular sieve catalyst at a temperature of from about 400° C. to 600° C., preferably from about 480° C. to about 550° C., at pressures of from atmospheric to 40 bar, and liquid hourly space velocities (LHSV) of from 0.1 $hr^{-1}$ to 15 $hr^{-1}$;

T) The adsorption of alkyl aromatic compounds for the purpose of separating various isomers of the compounds;

U) The conversion of oxygenates, e.g., alcohols, such as methanol, or ethers, such as dimethylether, or mixtures thereof to hydrocarbons including olefins and aromatics with reaction conditions including temperatures of from about 275° C. to about 600° C., pressures of from about 0.5 atmosphere to about 50 atmospheres, and a liquid hourly space velocity of from about 0.1 $hr^{-1}$ to about 100 $hr^{-1}$;

V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a molecular sieve catalyst at a temperature in the range of from about 250° C. to about 800° C., a LHSV of from about 0.2 $hr^{-1}$ to about 50 $hr^{-1}$, and a hydrocarbon partial pressure of from about 0.1 to about 50 atmospheres. Temperatures below about 250° C. may be used to oligomerize the feedstock when the feedstock is in the liquid phase when contacting the coated zeolite catalyst. Thus, when the olefin feedstock contacts the catalyst in the liquid phase, temperatures of from about 10° C. to about 250° C. may be used;

W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, reactor conditions include a temperature of from about 100° C. to about 760° C., a pressure of from about 0.1 atmosphere (bar) to about 200 atmospheres (bar), a weight hourly space velocity of from about 0.08 $hr^{-1}$ to about 2,000 $hr^{-1}$.

The separation processes of this invention are particularly suited to large, commercial scale reaction systems. For example, the separation processes of this invention are particularly suited to reaction systems that require a catalyst loading of at least about 1,000 kg of catalyst, based on total amount of catalyst located throughout the reaction system. In particular, the separation processes of this invention are particularly suited to reaction systems that require a catalyst loading of at least about 10,000 kg of catalyst, more particularly a catalyst loading of at least about 100,000 kg of catalyst, and most particularly a catalyst loading of at least about 250,000 kg of catalyst, based on total amount of catalyst located throughout the reaction system.

IV. Oxygenate to Olefin Reactions

An example of a reaction system that benefits from this invention is an oxygenate-to-olefin process. Conventionally, oxygenate-to-olefin processes are carried out in a fluidized bed, fast fluidized bed, or riser reactor configuration where a fluid (gas) flow of a feedstock is passed through a bed of solid catalyst particles. More generally, the processes of this invention are applicable to gas-solids reaction systems where the solids are separated from the gas flow at some point during the reaction process, including systems where the gas is inert. The examples below describe an oxygenate to olefin reaction system that can be improved using the separation process of the invention.

Oxygenates used in this invention include one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In another embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

In a conventional oxygenate to olefin reaction, a feed containing an oxygenate is contacted in a reaction zone of a reactor apparatus with a molecular sieve catalyst at process conditions effective to produce light olefins, i.e., an effective temperature, pressure, WHSV (weight hour space velocity) and, optionally, an effective amount of diluent, correlated to produce light olefins. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

The conversion of oxygenates to produce light olefins may be carried out in a variety of large scale catalytic reactors, including, but not limited to, fluid bed reactors and concurrent riser reactors as described in Fluidization Engineering, D. Kunii and O. Levenspiel, Robert E. Krieger Publishing Co. NY, 1977. Additionally, countercurrent free fall reactors may be used in the conversion process. See, for example, U.S. Pat. No. 4,068,136 and Fluidization and Fluid-Particle Systems, pages 48-59, F. A. Zenz and D. F. Othmer, Reinhold Publishing Corp., N.Y. 1960.

In one embodiment of this invention, the gas and solid particles are flowed through the gas-solids reactor system at a weight hourly space velocity (WHSV) of from about 1 $hr^{-1}$ to about 5,000 $hr^{-1}$, preferably from about 5 $hr^{-1}$ to about 3,000 $hr^{-1}$, more preferably from about 10 $hr^{-1}$ to about 1,500 $hr^{-1}$, and most preferably from about 20 $hr^{-1}$ to about 1,000 $hr^{-1}$. In one preferred embodiment, the WHSV is greater than 25 $hr^{-1}$, and up to about 500 $hr^{-1}$. In this invention, WHSV is defined as the total weight per hour of the gas flowing between reactor walls divided by the total weight of the solids flowing between the same segment of reactor walls. The WHSV is maintained at a level sufficient to keep the catalyst composition in a fluidized state within a reactor.

In another embodiment of the invention directed toward use of cyclones in conjunction with a riser reactor, the gas and solid particles are flowed through the gas-solids reactor system at a gas superficial velocity (GSV) at least 1 meter per second (m/sec), preferably greater than 2 m/sec, more preferably greater than 3 m/sec, and most preferably greater than 4 m/sec. The GSV should be sufficient to maintaining the solids in a fluidized state, particularly in a fast fluidized state.

In still another embodiment, cyclones configured according to this invention can be used with a fixed fluidized bed reactor. In such an embodiment, the GSV can be as low as 0.03 m/s.

In yet another embodiment of the invention, the solids particles and gas are flowed through the gas-solids reactor at a solids loading of at least 0.1 lb/ft$^3$ (1.6 kg/m$^3$), or at least 0.5 lb/ft$^3$ (8 kg/m$^3$), or at least 1.0 lb/ft$^3$ (16 kg/m$^3$), or at least 2.0 lb/ft$^3$ (32 kg/m$^3$), or at least 4.0 lb/ft$^3$ (64 kg/m$^3$). Alternatively, the solids loading can be 5 lb/ft$^3$ (80 kg/m$^3$) or less, or 4.0 lb/ft$^3$ (64 kg/m$^3$) or less, or 2.0 lb/ft$^3$ (32 kg/m$^3$) or less.

In one practical embodiment, the process is conducted as a fluidized bed process or high velocity fluidized bed process utilizing a reactor system, a regeneration system and a recovery system. In such a process the reactor system conveniently includes a fluid bed reactor system having a first reaction region consisting of various fast fluid or dense fluid beds in series or parallel and a second reaction region within at least one disengaging vessel, comprising two or more cyclones configured and/or operated according to various embodiments of the invention. In one embodiment, the fast fluid or dense fluid beds and disengaging vessel are contained within a single reactor vessel. Fresh feedstock, preferably containing one or more oxygenates, optionally with one or more diluent(s), is fed to the one or more fast fluid or dense fluid beds reactor(s) into which a molecular sieve catalyst composition or coked version thereof is introduced. In one embodiment, prior to being introduced to the reactor(s), the molecular sieve catalyst composition or coked version thereof is contacted with a liquid and/or vapor, preferably water and methanol, and a gas, for example, an inert gas such as nitrogen.

In an embodiment, the amount of fresh feedstock fed as a liquid and/or a vapor to the reactor system is in the range of from 0.1 weight percent to about 99.9 weight percent, such as from about 1 weight percent to about 99 weight percent, more typically from about 5 weight percent to about 95 weight percent based on the total weight of the feedstock including any diluent contained therein. The liquid and vapor feedstocks may be the same composition, or may contain varying proportions of the same or different feedstocks with the same or different diluents.

The process of this invention can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the process of this invention can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

In embodiments involving a riser reactor, the solids particles and gas are flowed through the gas-solids reactor at a solids to gas mass ratio of about 0.5:1 to about 75:1. Preferably, the solids particles and gas are flowed through the gas-solids reactor at a solids to gas mass ratio of about 8:1 to about 50:1, more preferably from about 10:1 to about 40:1.

During the conversion of a hydrocarbon feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

The feedstock entering the reactor system is preferably converted, partially or fully, in a reaction region into a gaseous effluent. In an embodiment, the reaction region is closely coupled to a plurality of separation devices, such as cyclone separators. In another embodiment, the gaseous effluent enters a disengaging vessel along with the coked catalyst composition. In such an embodiment, the disengaging vessel includes cyclone separators configured and/or operated according to the invention. In still another embodiment, the disengaging vessel also includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition. After exiting the separation devices and/or disengaging vessels, some or all of the catalyst can then introduced to a regeneration system.

In an embodiment, at least a portion of the coked catalyst composition is withdrawn from one or more of the disengaging vessels and introduced to the regeneration system. The regeneration system comprises a regenerator where the coked catalyst composition is contacted with a regeneration medium, preferably a gas containing oxygen, under conventional regeneration conditions of temperature, pressure and residence time. In an embodiment, a gas-solids flow exiting a regenerator may be passed through cyclones configured according to the invention. Alternatively, at least a portion of the catalyst can be flowed to bypass the regeneration system. The catalyst bypassing the regenerator can be flowed to another desired portion of the reaction system, such as flowing the catalyst directly into a catalyst cooler or allowing the catalyst to rejoin a fluidized bed in the reactor.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture).

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the reactor(s). In one embodiment, the regenerated catalyst composition withdrawn from the regeneration system is returned to the reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, 1997 (336-337).

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous reactor effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene (C2) splitter, propylene (C3) splitter and butene (C4) splitter.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Typically, in converting one or more oxygenates to olefin(s) having 2 or 3 carbon atoms, a minor amount hydrocarbons, particularly olefin(s), having 4 or more carbon atoms is also produced. The amount of $C_4+$ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products.

V. Description of Solid Particles

In an embodiment, the apparatus and method of the invention are generally useful for separating any solid particles in a gas-solids flow. In another embodiment, the solid particles can be catalyst particles, such as molecular sieve catalyst particles.

In an embodiment, a molecular sieve catalyst can characterized according to an Attrition Rate Index (ARI). The ARI methodology is similar to the conventional Davison Index method. The smaller the ARI, the more resistant to attrition; hence, the harder the catalyst. The ARI is measured by adding 6.0±0.1 g of catalyst, having a particle size ranging from 53 to 125 microns, into a hardened steel attrition cup. Approximately 23,700 scc/min of nitrogen gas is bubbled through a water-containing bubbler to humidify the nitrogen. The wet nitrogen is passed through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent catalyst that has broken apart through attrition.

The nitrogen flow passing through the attrition cup is maintained for 1 hour. Fines collected in the thimble are removed from the unit, and a new thimble installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in wt %/hr.

$$ARI = [C/(B+C)/D] \times 100\%$$

wherein

B=weight of catalyst left in the cup after the attrition test;
C=weight of collected fine catalyst particles after the first hour of attrition treatment; and
D=duration of treatment in hours after the first hour attrition treatment.

In an embodiment, the molecular sieve catalyst of this invention has an ARI of not greater than about 0.6 wt %/hr. Preferably, the molecular sieve catalyst has an ARI of not greater than about 0.5 wt %/hr, more preferably not greater than about 0.4 wt %/hr.

Molecular sieve catalyst particles for use in a gas-solids reaction can be synthesized by a variety of methods. In an embodiment, catalyst particles are synthesized by combining a first dried molecular sieve catalyst with water to make a water-catalyst composition, making a slurry from the water-catalyst composition, and drying the slurry to produce a second dried molecular sieve catalyst. The method particularly provides for the re-manufacturing, recycling or re-working of dried or substantially dried, or partially dried molecular sieve catalysts to yield catalyst particles with properties that are acceptable to the user or manufacturer. Such properties are usually observed after the dried molecular sieve catalyst is calcined. These properties include acceptable particle size, particle size distribution, particle density, and particle hardness.

The catalysts of this invention can include any of a variety of molecular sieve components. The components include zeolites or non-zeolites, preferably non-zeolites. In one embodiment, the molecular sieves are small pore non-zeolite molecular sieves having an average pore size of less than about 5 angstroms, preferably an average pore size ranging from about 3 to 5 angstroms, more preferably from 3.5 to 4.2 angstroms. These pore sizes are typical of molecular sieves having 8 membered rings.

Conventional crystalline aluminosilicate zeolites having catalytic activity are desirable molecular sieves that can be used in making the catalyst of this invention. Examples of such zeolite materials are described in U.S. Pat. Nos. 3,660, 274 and 3,944,482, both of which are incorporated herein by reference. Non-limiting examples of zeolites which can be employed in the practice of this invention, include both natural and synthetic zeolites. These zeolites include zeolites of the structural types included in the *Atlas of Zeolite Framework Types*, edited by Ch. Baerlocher, W. M. Meier, D. H. Olson, Fifth Revised edition, Elsevier, Amsterdam, 2001.

Zeolites typically have silica-to-alumina $(SiO_2/Al_2O_3)$ mole ratios of at least about 2, and have uniform pore diameters from about 3 to 15 Angstroms. They also generally contain alkali metal cations, such as sodium and/or potassium and/or alkaline earth metal cations, such as magnesium and/or calcium. In order to increase the catalytic activity of the zeolite, it may be desirable to decrease the alkali metal content of the crystalline zeolite to less than about 5 wt. %, preferably less than about 1 wt. %, and more preferably less than about 0.5 wt. %. The alkali metal content reduction, as is known in the art, may be conducted by exchange with one or more cations selected from the Groups IIB through VIII of the Periodic Table of Elements (the Periodic Table of Elements referred to herein is given in *Handbook of Chemistry and Physics*, published by the Chemical Rubber Publishing Company, Cleveland, Ohio, 45th Edition, 1964 or 73rd Edition, 1992), as well as with hydronium ions or basic adducts of hydronium ions, e.g., $NH_4^+$, capable of conversion to a hydrogen cation upon calcination. Desired cations include rare earth cations, calcium, magnesium, hydrogen and mixtures thereof. Ion-exchange methods are well known in the art and are described, for example, in U.S. Pat. Nos. 3,140,249; 3,142,251 and 1,423,353.

In another embodiment, the catalyst particles which are flowed through the gas-solids reactor system of this invention are molecular sieve catalysts, such as a conventional molecular sieve. Examples include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof, and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice*, Second Completely Revised and Expanded Edition, Volume 137, pages 1-67, Elsevier Science, B.V., Amsterdam, Netherlands (2001).

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. Pat. No. 6,743,747 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992).

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO molecular sieves useful herein include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56 and metal containing molecular sieves thereof. Of these, particularly useful molecular sieves are SAPO-18, SAPO-34, SAPO-35, SAPO-44, SAPO-56 and metal containing derivatives thereof. SAPO-34 is particularly preferred.

In another embodiment of the invention, the catalyst used in this invention incorporates aluminophosphate (AlPO) molecular sieves. These molecular sieves can be included as separate crystals or they can be intermixed with other crystalline structures such as by an intergrowth structure. Examples of aluminophosphates include AlPO-5, AlPO-11, AlPO-18, AlPO-31, AlPO-34, AlPO-36, AlPO-37 and AlPO-46.

In one embodiment, the catalyst includes a combination of at least one SAPO and at least one AlPO molecular sieve, wherein the SAPO is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47 and SAPO-56, and the AlPO is selected from the group consisting of AlPO-5, AlPO-11, AlPO-18, AlPO-31, AlPO-34, AlPO-36, AlPO-37 and AlPO-46. The sieves can be combined as separate crystals or as intergrown crystals. Preferably, the SAPO is SAPO-18 or SAPO-34, and preferably, the AlPO is AlPO-34 or AlPO-18.

Additional examples of intergrowth molecular sieves useful in this invention include those described in U.S. Patent Application Publication No. 2002-0165089 and International Publication No. WO 98/15496, published Apr. 16, 1998. Note that SAPO-18, AlPO-18 and RUW-18 have an AEI framework-type, and SAPO-34 has a CHA framework-type, and that preferred molecular sieves used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are desired. Particularly desired are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

VI. Experimental Comparison of Close Coupling Termination Devices

Figure 7:
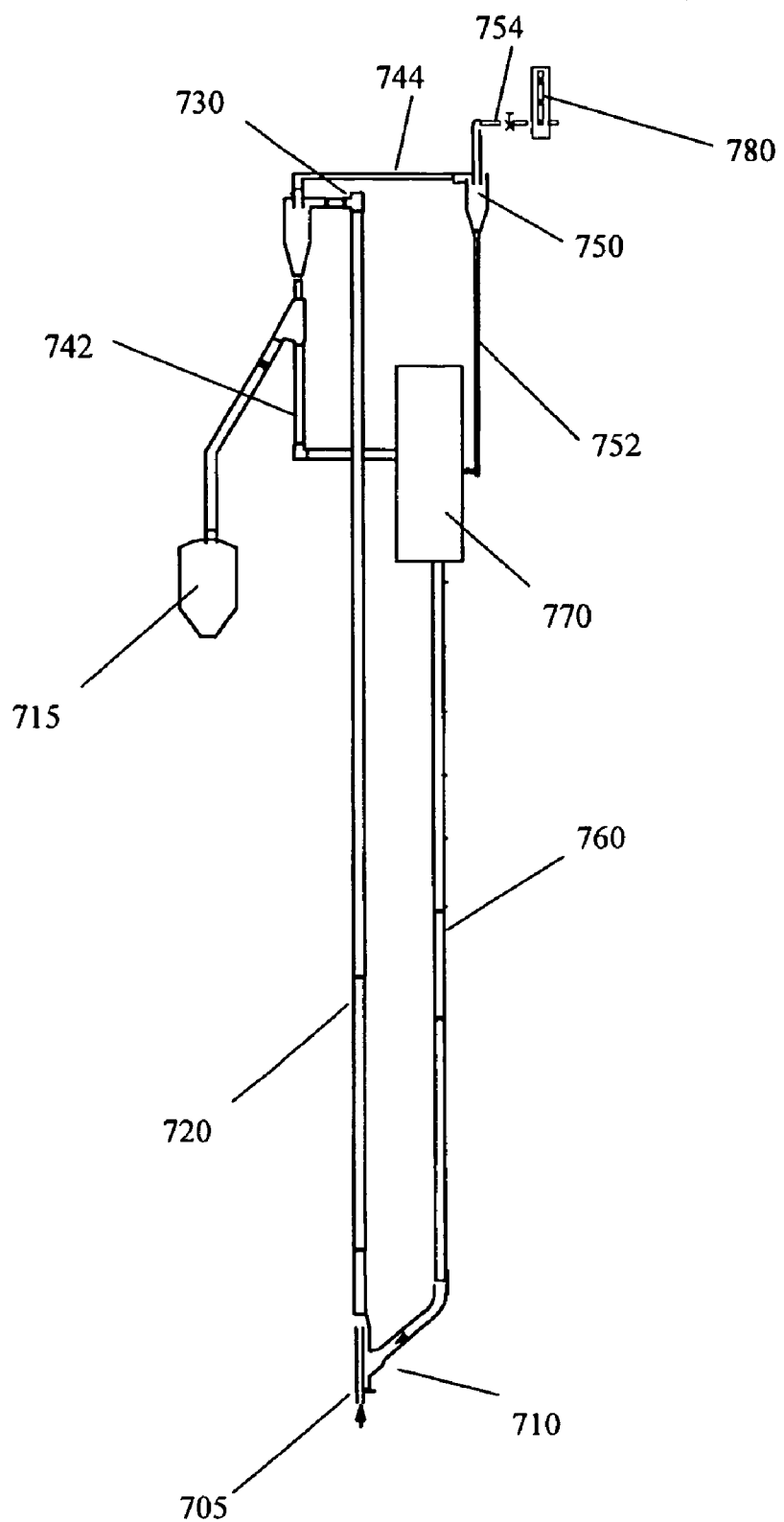
FIG. 7 depicts a testing apparatus for comparative testing of termination devices.

FIG. 7 schematically depicts an experimental test apparatus for investigating variations in solid particle attrition and losses due to changes in conduits used for coupling a riser to a separation device. The apparatus in FIG. 7 represents a continuous flow reactor for circulating catalyst using air as a gas. Air enters the apparatus via 6 inch (15 cm) inlet 705 in 10 inch (25 cm) bottom pot 710. As the air rises into 8 inch (20 cm) riser 720, the air mixes with catalyst to form gas-solids flow. The gas-solids flow rises through riser 720 until it reaches termination device 730. Termination device 730 provides a close coupling between riser 720 and first stage cyclone 740. Upon entering first stage cyclone 740, the gas-solids flow is separated into a lower density (primarily gas) flow and a higher density (primarily solids) flow. The higher density flow exits via dipleg 742 and enters collection vessel 770. The lower density flow is passed into second stage cyclone 750 via conduit 744. The higher density flow from second stage cyclone 750 also exits via a dipleg 752 and enter collection vessel 770. The lower density flow leaves the apparatus via conduit 754. After entering collection vessel 770, the solids are returned to bottom pot 710 via standpipe 760 for further circulation in the test apparatus.

Solids can be initially added into the test apparatus via collection vessel 770. The solids are then circulated through the test apparatus for a period of time. Any solids still remaining in the flow in conduit 754 (after passing through second stage cyclone 750) are collected in baghouse 780. The collected solids in baghouse 780 are used to characterize the effects of the different close coupling conduits on the attrition and loss rate in test apparatus. The weight of solids remaining in the test apparatus can be determined by diverting the solids flow into receiving tank 715.

Figure 8:
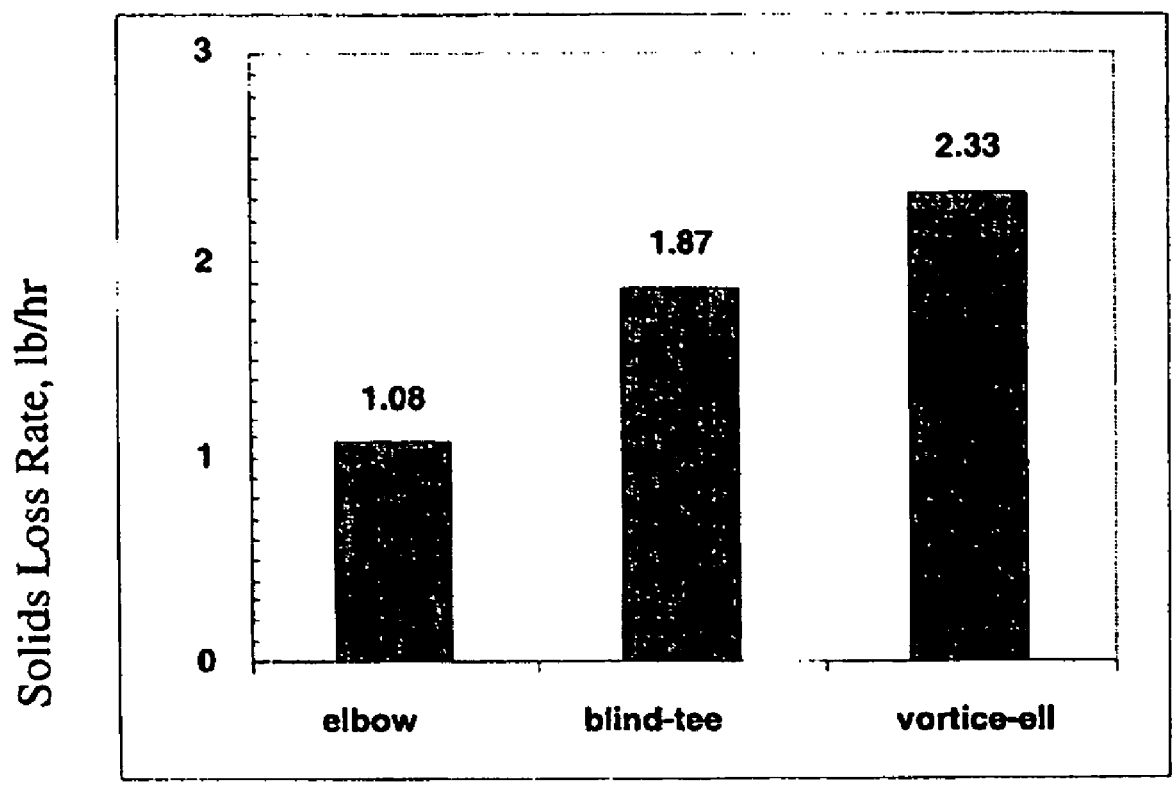
FIG. 8 depicts comparative results of catalyst losses for various termination devices.

FIG. 8 depicts results generated using the test apparatus shown in FIG. 7. The results in FIG. 7 show the change in catalyst losses for 3 different types of close coupling termination devices 730. Each of the termination devices provides a 90° change in the flow direction of the gas-solids flow. The superficial gas velocity in the riser during the tests was 55 ft/sec (17 m/s). The solids loading during the tests was 1.6 lb/ft$^3$ (roughly 25.6 kg/m$^3$), which is representative of a typical loading for a gas-solids reaction in a commercial reactor. A FCC catalyst was used as the solid catalyst in the test reactor.

The first bar in FIG. 8 corresponds to an elbow conduit in accordance with the invention. The ratio of the radius of curvature of the elbow conduit versus the diameter of the riser is 2. The second and third bars in FIG. 8 correspond to "blind-tee" and "vortice-ell" configurations, respectively. In a blind-tee, a riser is terminated using a sharp 90° turn just below the top of the riser conduit, which leaves a small rectangular volume above the conduit exiting the riser at 90°. A vortice-ell termination has a similar geometry to a blind-tee, with the exception that the small volume above the 90° exit conduit has a hemispherical shape.

FIG. 8 shows that the elbow conduit according to an embodiment of the invention provides the lowest level of catalyst loss at 1.08 lbs/hr (0.5 kg/hr). The blind-tee terminator produced a catalyst loss of 1.87 lbs/hr (0.8 kg/hr), while the vortice-ell produces a catalyst loss of 2.33 lbs/hr (about 1 kg/hr). Note that the vortice-ell terminator showed improved performance at lower catalyst loadings.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

We claim:

1. A method for separating solids from a gas-solids flow comprising:

flowing a gas-solids flow in a riser, the top of the riser being joined to a plurality of termination devices at a solids loading of at least 1.0 lb/ft$^3$ (16 kg/m$^3$) and a superficial gas velocity of greater than 4 m/s;

passing the gas-solids flow through the plurality of termination devices into one or more separation devices, the radius of curvature of each termination device being from about 1.0 to 5 times greater than the diameter of the termination device;

changing the direction of the gas-solids flow by at least 90° by flowing the gas-solids flow through the plurality of termination devices wherein the termination devices comprise cap terminators having vent gaps;

allowing vapors from the gas-solids flow to escape through a vent gap placed between the riser termination device and the first separation device or vent placed between the first and second separation devices; and separating the gas-solids flow into a lower density flow and a higher density flow in the one or more separation devices;

wherein the plurality of termination devices closely couple the riser to the separation devices and are substantially sealed, and the combined cross-sectional area of the termination devices is at least 100% of the cross-sectional area of the riser but 350% or less of the cross-sectional area of the riser.

2. The method of claim 1, wherein each termination device closely couples the riser to a different separation device.

3. The method of claim 1, wherein flowing the gas-solids flow in a riser comprises contacting an oxygenate feedstock with a molecular sieve catalyst.

4. The method of claim 3, wherein the molecular sieve catalyst comprises a silicoaluminophosphate catalyst.

5. The method of claim 1, wherein the one or more separation devices comprise cyclone separators.

6. The method of claim 1, wherein the separation devices are openly coupled to the riser via the termination devices.

7. The method of claim 6, wherein the termination devices comprise arcuate conduits.

8. A method for separating solids from a gas-solids flow, comprising:

flowing a gas-solids flow in a riser, the top of the riser being joined to a plurality of termination devices at a solids loading of at least 1.0 lb/ft$^3$ (16 kg/m$^3$) and a superficial gas velocity of greater than 4 m/s;

passing the gas-solids flow out of the riser and through a plurality of termination devices that openly couple the riser to one or more separation devices, the combined cross-sectional area of the termination devices being at least 100% of the cross-sectional area of the riser;

changing the direction of the gas-solids flow by at least 90° by flowing the gas-solids flow through the plurality of termination devices;

allowing vapors from the gas-solids flow to escape through a vent gap placed between the riser termination device and the first separation device or vent placed between the first and second separation devices; and separating the gas-solids flow into a higher density flow and a lower density flow in the one or more separation devices;

wherein the plurality of termination devices closely couple the riser to the separation devices and are substantially sealed, and the combined cross-sectional area of the termination devices is at least 175% of the cross-sectional area of the riser but 300% or less of the cross-sectional area of the riser.

9. The method of claim 8, wherein flowing the gas-solids flow in a riser comprises contacting an oxygenate feedstock with a molecular sieve catalyst.

10. The method of claim 9, wherein the molecular sieve catalyst comprises a silicoaluminophosphate catalyst.

11. The method of claim 9, wherein the molecular sieve catalyst comprises a catalyst with an attrition resistance index of not greater than 0.6 wt %/hr.

12. The method of claim 8, wherein the termination device comprises at least one curved surface.

13. The method of claim 1, wherein the radius of curvature of each termination device being from about 1.75 to 5 times greater than the diameter of the termination device.

* * * * *